United States Patent [19]
Kunz et al.

[11] Patent Number: 4,929,671
[45] Date of Patent: May 29, 1990

[54] ALLYLIC SIDE CHAIN-CONTAINING SOLID PHASE SYSTEMS, PROCESSES FOR THE PREPARATION THEREOF AND THE USE THEREOF IN SOLID PHASE REACTIONS

[75] Inventors: Horst Kunz, Mainz-Drais; Berthold Dombo, Wiesbaden-Medenbach, both of Fed. Rep. of Germany

[73] Assignee: Orpengen Medizinisch-Molekularbiologische Forschungsgesellschaft mbH, Heidelberg, Fed. Rep. of Germany

[21] Appl. No.: 205,453

[22] Filed: Jun. 10, 1988

[30] Foreign Application Priority Data

Jun. 19, 1987 [DE] Fed. Rep. of Germany ....... 3720269
Feb. 5, 1988 [DE] Fed. Rep. of Germany ....... 3803545

[51] Int. Cl.$^5$ .................... C07K 1/04; C07K 17/06; C07K 17/08; C07K 17/14
[52] U.S. Cl. .................... 525/54.11; 525/326; 525/327; 525/329; 525/333.3; 525/288; 530/333; 530/334
[58] Field of Search .................... 525/54.1, 54.11, 326, 525/327, 329, 333.3; 530/333, 334

[56] References Cited

U.S. PATENT DOCUMENTS

| | | | |
|---|---|---|---|
| 3,826,767 | 7/1974 | Hoover et al. | 527/314 |
| 3,846,265 | 11/1974 | Yamaguchi et al. | 527/314 |
| 4,045,595 | 8/1977 | Chiu et al. | 527/314 |

OTHER PUBLICATIONS

Eur. J. Biochem 74, 1-6 (1977) "Abbreviations and Symbols".
Mitchell et al., "Preparation of Aminomethyl–Polystyrene Resin by Direct Amidomethylation" *Tet Lett* No. 42, pp. 3795-3798, 1976.

*Primary Examiner*—John Kight, III
*Assistant Examiner*—Nathan M. Nutter
*Attorney, Agent, or Firm*—Felfe & Lynch

[57] ABSTRACT

The present invention provides an allylic side chain-containing solid phase system, in which the allylic side chains are bound to a solid carrier material, of the general formula

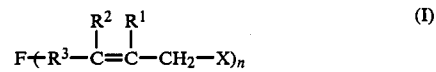

$$F\!+\!R^3\!-\!\underset{|}{C}\!=\!\underset{|}{\overset{R^2\;R^1}{C}}\!-\!CH_2\!-\!X)_n \qquad (I)$$

wherein F is a solid carrier material, $R^1$ and $R^2$, which can be the same or different, are hydrogen or halogen atoms or alkyl or aryl radicals, $R^3$ is a linking grouping (spacer), X is a hydroxyl group, a halogen atom, a sulphonate or phosphonate group or an acyloxy radical, acyl in the acyloxy radical being the residue of an aliphatic carboxylic acid or the radical RCO—, R being an organic radical, which is bound via the carbonyl group, and n is the number of side chains bound to the carrier material.

The present invention also provides processes for the preparation of these solid phase systems and is also concerned with the use thereof for solid phase reactions.

21 Claims, No Drawings

ALLYLIC SIDE CHAIN-CONTAINING SOLID PHASE SYSTEMS, PROCESSES FOR THE PREPARATION THEREOF AND THE USE THEREOF IN SOLID PHASE REACTIONS

The present invention is concerned with solid phase systems which contain allylic side chains, processes for the preparation thereof and the use thereof in solid phase reactions, especially for the solid phase synthesis of peptides, glycopeptides or proteins.

The increased demands made of pharmaceuticals, foodstuff additives and other active materials with respect to their selectivity of action, compatibility and biodegradability has, in turn, made precision synthesis of peptides very important. In spite of the now highly developed gene-technological techniques, this also applies to the chemical synthesis of peptides this is the only technique which makes it possible to prepare, for example, peptides with non-natural constructional units and structural elements.

For the chemical preparation of peptides, the introduction of the solid phase synthesis according to R. B. Merrifield (R. B. Merrifield, J. Am. Chem. Soc., 85, 2149/1963) signified a great advance. This is still true in spite of problems recognised since then. These problems appear repeatedly in the case of these solid phase peptide syntheses and concern the purity of the synthesised products.

In known prior art solid phase syntheses, one used, as C-terminal protective and anchor groups, substituted benzyl esters which permit the removal of the synthesised peptides from the polymeric carrier under more or less strongly acidic conditions. The acidic cleavage conditions (in the classical Merrifield synthesis either, hydrogen bromide in various solvents or hydrogen fluoride is used) have the disadvantage that undesired side reactions, such as transpeptidation or transalkylation, can occur. The synthesis of glycopeptides can scarcely be carried out in this way because the sensitive glycosidic bonds of these molecules are cleaved or anomerised under acidic conditions (with regard to the glycopeptide synthesis cf. for example H. Kunz (Angewandte Chemie, 99 (1987); Angew. Chemie, Int. English edition, 26, 294/1987).

It is an object of the present invention to provide solid phase systems, useful for solid phase synthesis of peptides and glycopeptides, in which the peptides and glycopeptides can be selectively split off from the polymeric carrier and under such mild conditions that no cleavage of the glycosidic bonds or anomerisations occur.

Thus, according to the present invention, there is provided an allylic side chain-containing solid phase system, in which the allylic side chains are bound to a solid carrier material, of the general formula

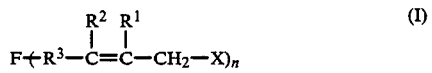

(I)

wherein F is a solid carrier material, $R^1$ and $R^2$, which can be the same or different, are hydrogen or halogen atoms or alkyl or aryl radicals, $R^3$ is a linking groups (spacer), X is a hydroxyl group, a halogen atom, a sulphonate or phosphonate group or an acyloxy radical, acyl in the acyloxy radical being the residue of an aliphatic carboxylic acid or the radical RCO—, R being an organic radical, is bound via the carbonyl group, and RCO— is especially a protected or unprotected residue of an amino acid, peptide, glycopeptide or nucleotide or of a hydroxycarboxylic, dicarboxylic or tricarboxylic acid, and n is the number of side chains bound to the carrier material.

The alkyl radical $R^1$ or $R^2$ can be straight-chained or branched and preferably contains up to 7 carbon atoms and especially preferably up to 3 carbon atoms.

An aryl radical $R^1$ or $R^2$ is preferably a substituted or unsubstituted mono- or dicyclic aryl radical, for example naphthyl-(1) or -(2) especially preferred is the phenyl radical. The aryl radical can be substituted by one or more substituents, for example lower alkyl radicals and/or halogen atoms, but is preferably unsubstituted. Two alkyl substituents can, together with the aryl radical, also form a system of two or more rings, for example tetrahydronaphthalene.

Halogen can be fluorine, chlorine, bromine or iodine and is preferably, especially in the definition of X, chlorine or bromine.

The radical R is a linking group (spacer, link) and is, for example, one of the spacer groupings previously known as usefull in solid phase technique (Merrifield technique) (for example CASET, CAMET; cf. for example Rompps Chemie-Lexikon, 8th edition, page 2543). The nature of $R_3$ depends on several factors. Especially important is the process used for the preparation of the solid phase system, as described infra. Other especially important factors include the nature of the carrier material, the functional groups present on the carrier material (referred to as "A" and "B" hereafter), and the compounds containing the alkyl group. The radical $R^3$ can be, for example, an alkylene, aralkylene or arylene radical which can contain polar groups on one or both ends. When polystyrene is used as carrier material, R3 can be, for example, a —$CH_2$—NHCO—group.

In an acyloxy radical X, in which acyl is the residue of an aliphatic carboxylic acid, acyl is preferably the acid residue of an aliphatic carboxylic acid containing up to 7 and preferably up to 4 carbon atoms, for example formyl, acetyl and propionyl.

For the solid carrier material, it is preferable to start with one which has functional groups which are well suited for the reaction with the compound carrying the allyl grouping, in which case the spacer grouping $R^3$ can be formed during this reaction or can also be partly or wholly a component (substituent) of the solid carrier material.

The carrier material is preferably an organic or inorganic polymer, for example a synthetic, semisynthetic or natural polymer. Such polymers include, for example, cross-linked polyacrylamides, methacrylates, dextrans (for example those known under the Registered Trade Mark "Sephadex"), cellulose, and especially polystyrene. However, the carrier material can also be a solid base material which is coated with a material appropriate for linking with the allyl side chains, for example with an appropriate polymer or a cross-linked protein. The base material can be, for example, glass, silica gel or also a synthetic resin. Organic polymers which are appropriate for the carrier material and as coating are preferably polyacrylamides, polyethyleneglycol and especially polystyrene.

For the formation of an appropriate spacer grouping $R^3$, it is be desirable to use, for example, a polystyrene substituted with aminomethyl radicals. In the solid phase system according to the present invention, the aminomethyl radicals are then preferably sulstituted by a —CO—$(CH_2)_n$—C($R^2$)=C($R^1$)—$CH_2$—X radical, where n is 0 or a whole number of preferably up to 10 and especially up to 7.

The present invention also provides a process for the preparation of compounds of general formula (I), in which X is a hydroxyl group, a halogen atom, a sulphonate or phosphonate group or an acyloxy radical which is the the residue of an aliphatic carboxylic acid, wherein a solid carrier material, which contains functional groups A appropriate for linking with the allyl radical C($R^2$)=C($R^1$)=$CH_2$=X, is reacted with a compound of the general formula B—C($R^2$)=C($R^1$)=$CH_2$=X, A and B being groups which react with one another by condensation and/or addition with the formation of a linkage between the solid carrier material and the allyl radical.

The groups A and B are those which react by condensation and/or addition with the formation of a linkage between the carrier material and the allyl groups Such groupings are preferably those usually employed in condensation and addition reactions, such as amino groups, for example in the form of aminomethyl radicals, halogen atoms, ester groups, nitrile groups and the like. The condensation and/or addition reactions can, as a rule, be carried out in known manner, for example with the splitting off of water, a hydrogen halide or the like.

In a preferred embodiment form, for example a polystyrene containing aminomethyl radical (groups A) is reacted with a terminally allylic-substituted unsaturated carboxylic acid or a carboxylic acid derivative or with an 1,3-allyl isomer thereof with formation of an amide grouping. An allylic unsaturated carboxylic acid can be, for example, 4-bromocrotonic acid (B =Br) in which, after the reaction with amide group formation, the COOH group is converted, for example, into a —$CH_2Br$ group (X =Br).

Further allylic unsaturated carboxylic acids include, for example, 4-halo-, 4-hydroxy-, 4-acyloxyand 4-sulphonyloxy-crotonic acids.

The present invention also provides a process for the preparation of compounds of general formula (I), in which X is an acyloxy radical in which the acyl moiety RCO— is a protected or unprotected residue of an amino acid, peptide, glycopeptide or nucleotide, especially an oligonucleotide, or of a hydroxycarboxylic, dicarboxylic or tricarboxylic acid, wherein a solid phase system of general formula (I), in which X is a hydroxyl group, a halogen atom, a sulphonate or phosphonate group or an acyloxy radical, acyl being the residue of an aliphatic carboxylic acid, is reacted with an N-protected amino acid, peptide, glycopeptide or nucleotide or with a hydroxycarboxylic, dicarboxylic or tricarboxylic acid or a derivative or salt thereof, whereafter the N-terminal protective groups are optionally split off. By a peptide residue, there is thereby to be understood, quite generally, also the residue of a protein, for example of an enzyme.

The reaction with the N-protected amino acids, peptides, glycopeptides, nucleotides or hydroxycarboxylic, dicarboxylic or tricarboxylic acids or derivatives or salts thereof can take place in known manner, for example, as is usual in the conventional solid phase technique (Merrifield technique). As protective groups there can thereby be used the conventionally employed protective groups, for example benzyloxycarbonyl, tert. butyloxycarbonyl, 3,5-dimethoxyphenyl-2,2-propyloxycarbonyl,trityl,4-biphenyl-2-propyloxycarbonyl, tert. butyl ester, benzyl ester, 2 nitrophenylsulfenyl, or flurenylmethyloxycarbonyl.

The C-terminal protective (anchor) groups used in the solid phase systems and processes according to the present invention, via which the amino acids, peptides, glycopeptides and the like are bound to the polymeric carrier, are of the allyl ester type. Allyl esters can, as C-terminal protective groups in glycopeptide, nucleotide and peptide syntheses, be split off selectively and under mild, almost neutral conditions from the blocked compounds (cf. H. Kunz, Angew. Chemie, 99, 297/1987). This is achieved by noble metal catalysis, for example by catalysis with compounds of the platinum group of metals, such as ruthenium, rhodium, palladium, osmium, iridium and platinum, and especially by catalysis with rhodium (I) compounds (cf. H. Waldmann and H. Kurz, Liebigs Ann. Chem., 1983, 1712) or with reactions catalysed by palladium (0) compounds (H. Kunz and H. Waldmann, Angew. Chemie, 96, 47/1984; Angew. Chemie Int. Engl. Ed., 23, 71/1984; H. Kunz an- C. Unverzagt, Angew. Chemie, 96, 426/1984; Angew. Chemie, Int. Engl. Ed., 23, 436/1984). By means of the transfer of this deblocking methodology to the solid phase peptide synthesis, that the removal of the peptide, glycopeptide or nucleotide chain built on to the carrier is now possible under practically neutral conditions.

Therefore, the present invention also provides a process for the synthesis of unprotected or partly protected peptides, glycopeptides, nucleotides, hydroxycarboxylic acids, dicarboxylic acids and tricarboxylic acids, wherein, from a compound of general formula (I), in which X is an acyloxy radical, in which the acyl radical RCO—is a protected or unprotected residue of a peptide, glycopeptide, nucleotide, hydroxycarboxylic acid, dicarboxylic acid or tricarboxylic acid, the acyl radical RCO—is split off in the presence of a catalytic amount of a platinum metal compound.

The splitting off in the presence of a catalytic amount of a compound of the platinum group metals, preferably in the presence of a rhodium (I) compound and especially in the presence of a palladium (O) compound, can be carried out in a solvent or solvent system appropriate therefor, for example in tetrahydrofuran, in the presence of an appropriate nucleophil, for example morpholine, dimedone or some other easily deprotonisable CH acid compound. The reaction is preferably carried out at ambient temperature with the exclusion of oxygen.

Because of the extraordinarily mild cleavage conditions, according to the present invention, it is possible to carry out the splitting off of the peptides, glycopeptides, nucleotides and other residues selectively and without cleavage of glycosidic bonds or of anomerisations or isomerisations.

Besides their use in solid phase technology (Merrifield technology) for peptide synthesis or glycopeptide synthesis, the solid phase systems according to the present invention can also be used as solid phases in other solid phase techniques, for example for the synthesis of oligonucleotides, which can possibly be further elongated enzymatically, for example to give certain DNA sequences, for sequence analyses but also in the case of reactions in which enzymes, catalytically-acting Lewis acids, redox systems and the like are brought into solid form by immobilisation as a result of adsorption, polymerisation, grafting or the like, which simplifies the dosaging, further working up and separation from reaction products. In addition, a used in solid bed processes is also possible (cf. for example Rompps Chemie-Lexikon, 8th edition, pages 1263 and 2543).

Therefore, the present invention is also concerned with the use of a solid phase system according to the present invention of general formula (I), wherein X is a hydroxyl group, a halogen atom, a sulphonate or phosphonate group or an acyloxy radical, in which the acyl moiety is the residue of an aliphatic carboxylic acid, for solid phase reactions and especially for the solid phase synthesis of peptides, glycopeptides, nucleotides and proteins, for example of enzymes.

In the following are described some preferred embodiments forms of solid phase systems according to the present invention, processes for the preparation thereof and the use thereof.

Synthesis of polymeric carriers with allylic anchor groups

For the synthesis of polymers of general formula (I) with side chains which carry allylic groups, various ways can be used. The principle procedure is shown with a commercially available (Bio-Rad, Bio-Beads S-X1 1.28 mg. Cl$_2$/g.) chloromethylated polystyrene 1 which is first converted in known manner (A. R. Mitchell et al., J. Am. Chem. Soc., 98, 7337/1976) with potassium phthalimide, via the phthaloylamido derivative 2, into the aminomethylpolystyrene 3.

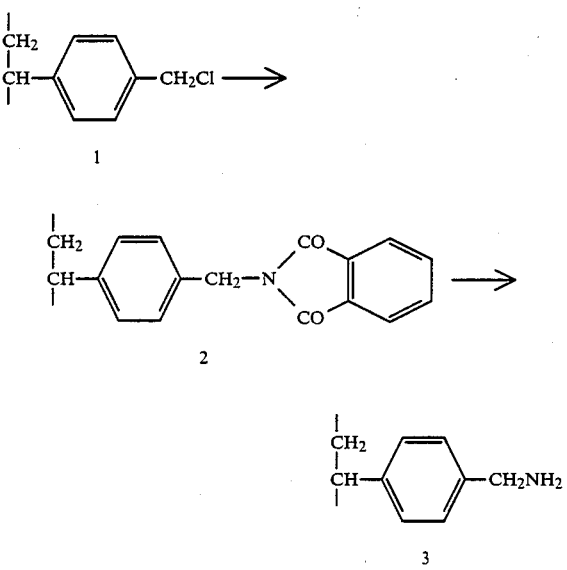

Alternatively, the intermediate stage 2 can also be prepared in known manner (R. B. Merrifield et al., Tetrahedron Lett., 42, 3795/1976) from appropriate crosslinked polystyrene by reaction with N-(chloromethyl)phthalimide.

The conversion of 2 into 3 is carried out with hydrazine in ethanol (see E. R. Mitchell et al., loc. cit.).

As an example for a polymeric carrier with amino groups, the aminomethylate polystyrene 3 is now converted into a compound of the general formula (I) by reacting it with an acyl or alkyl compound which carries a terminal allyl halide, ester or alcohol grouping. As an example, in the following there is described the reaction of the resin 3 with 4-bromocrotonic acid 4 (see K. Ziegler et al., Liebigs Ann. Chem., 551, 117/1942). The linking is achieved, for example, with the help of dicyclohexylcarbodiimide (DCC) in the presence of 4-dimethylaminopyridine (DMAP) (Example 1) or with DCC/1-hydroxybenzotriazole in dichloromethane (cf. W. Konig and R. Geiger, Chem. Ber., 103, 788/1970).

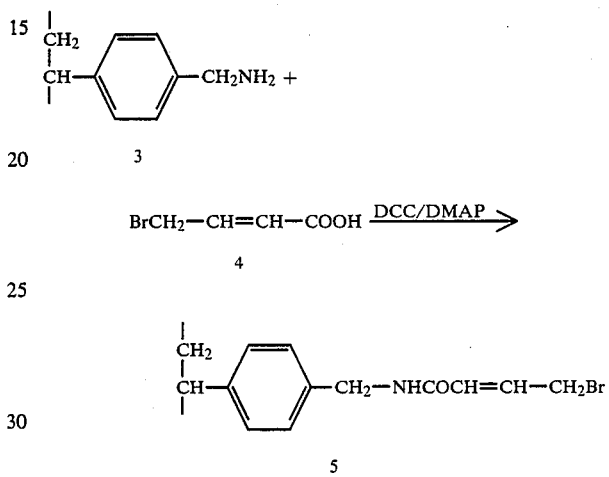

Instead of bromocrotonic acid 4, in the same way there can be used longer-chained allylic substituted alkene-carboxylic acids, for example of the general formula $X—CH_2—CH=CH—(CH_2)_x—COOH$, in which X is a bromine atom and is, for example, 0 or 7 (in the latter case, for example, in admixture with 9-bromo-10-undecenoic acid). In the same way, in analogous reactions with hydroxymethylated polymers instead of 3 to 5, there are obtained analogous esters.

Compound 5 is an example of a compound of general formula (I) in which X is a bromine atom. In analogous way, starting from a compound 3 and corresponding conversion of the carboxyl group or subsequent conversion of bromine in compound 5, there can be prepared compounds of general formula (I) in which X is a halogen atom, a hydroxyl, sulphonate or phosphonate group or an acyloxy radical, the acyl moiety of which is the residue of an aliphatic carboxylic acid.

Coupling on of the C-terminal amino acid to a carrier according to the present invention By the reaction of salts and especially of cesium salts of N-protected amino acids 6 with resins of the type 5, the C-terminal amino acids of the peptide or glycopeptide to be synthesised are coupled on to the polymeric carrier. The coupling products, thereby formed, such as 7, correspond to the general formula (I) (Example 2 for alanine). The yields are 70–85%. For the following N-protected amino acids 6, there are obtained the indicated yields: Boc-Ala 82%; Boc-Leu Boc-Ile 70% and Z-Ala 80%).

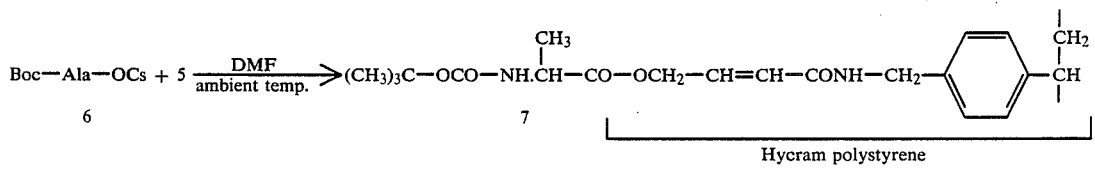

The N-terminal protective group can be split off selectively from the amino acid bound to the polymeric carrier in 7 as (substituted) allyl ester. In the case of the tert.-butyloxycarbonyl (Boc) group (for example in 7), 538; S. S. Wang, J. Am. Chem. Soc., 95, 1328/1973). There is thus obtained, for example, from 8, after deproteinisation and coupling with Boc-leucine, the bound dipeptide 9 (Example 4).

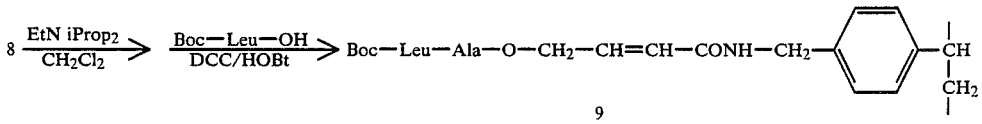

this takes place by treatment with trifluoroacetic acid (Example 3). The allyl ester bond on the carrier remains completely stable.

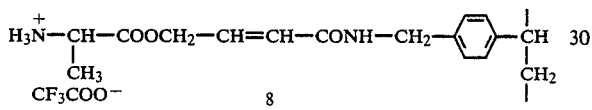

the bound amino acid hydrosalts, such as 8, there is obtained the free amino compound with tertiary bases. If, instead of the Boc group, there is used an amino protective group which can be split off under neutral or basic conditions, for example the fluorenylmethoxycarbonyl (Fmoc) radical which can be split off under neutral or basic conditions, on with morpholine or piperidine/dichloromethane, then a free, polymer-bound amino compound is formed directly.

Peptide and glycopeptide syntheses on the carrier according to the invention

On these N-unblocked substances there is now carried out the build up of the peptide chain according to the methods known in the solid phase peptide syntheses (cf. for example, R. B. Merrifield, E. Girali et al., Synthesis, 1985, 181; Ch. Birr, "Aspects of the Merrifield Peptide Synthesis" in "Reactivity and Structure Concepts in Organic Chemistry", Vol. 8, ed. K. Hafner et al., pub. Springer-Verlag, Berlin- Heidelberg-New York, 1978; J. Lenard and A. B. Robinson, J. Am. Chem. Soc., 89, 181/1967; S. Sakakibara and Y. Shimonishi, Bull. Chem. Soc. Japan, 38, 1412/1965; E. Atherton et al., J. Chem. Soc., Perkin Trans. I, 1981, By fixing Boc-isoleucine on the polymeric carrier according to the present invention, such as of type 5, and by two subsequent synthesis cycles, consisting of N-terminal protective group splitting off, liberation of the terminal amino group and chain lengthening. a) with $N^2$-tert.-butyloxycarbonyl-$N^4$-(2-acetamido-3,4,6-tri-0-acetyl-2-desoxy--D-glucopyranosyl)-asparagine and b) with Boc-leucone, there is synthesised the glycotripeptide 10 in solid phase-bound form (Example 5).

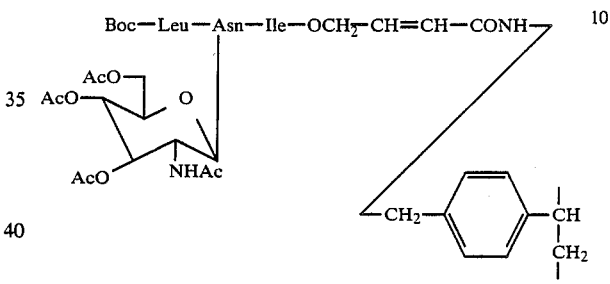

As a further illustrative example, by the process according to the present invention. there is built up the peptide active material Leu-encephaline in solid phase-bound form 11 (Example 6).

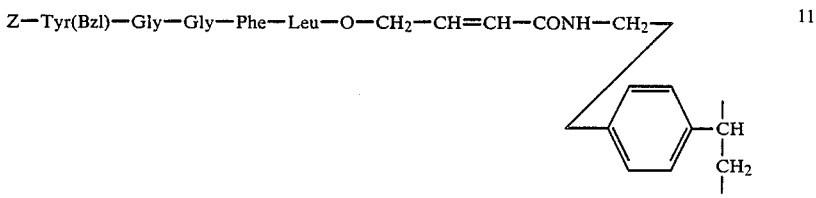

Splitting off of peptides and glycopeptides from the carrier according to the present invention The special feature of the polymeric carriers according to the present invention and of the solid phase syntheses carried out therewith is the unbinding of the amino acids, peptides and glycopeptides as allylic esters (for example in compounds 8, 9, 10 and 11). From this there is obtained the decisive advantage that the synthesised peptides and glycopeptides can be split off from the carrier under very mild, practically neutral conditions. This splitting off can be achieved, for example, by treatment of the polymer-bound derivatives with catalytic amounts of a palladium (O) catalyst, with the exclusion of oxygen, in tetrahydrofuran or some other solvent system in the presence of an appropriate nucleophile, such as morpholine, dimedone or some other easily deprotonisable CH acidic compound. As a rule, the reaction takes place completely at ambient temperature in a few hours. Due to the extraordinarily mild splitting off conditions, even sensitive structures, for example the glycosidic bonds, and protective groups, for example the Boc and Z protective groups, are dependably contained in the dissolved off peptide, for example peptides 12 and 14 or glycopeptide, for example glycopeptide 13.

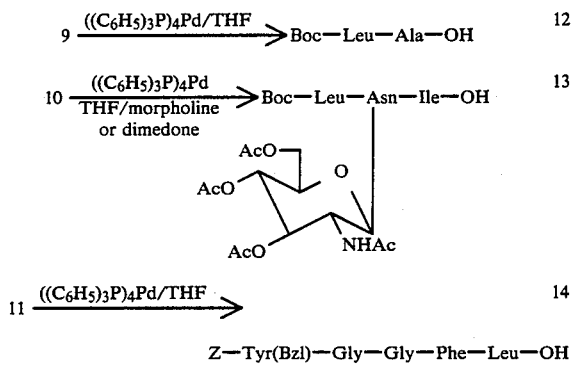

9 $\xrightarrow{((C_6H_5)_3P)_4Pd/THF}$ Boc—Leu—Ala—OH    12

10 $\xrightarrow[\text{or dimedone}]{((C_6H_5)_3P)_4Pd \text{ THF/morpholine}}$ Boc—Leu—Asn—Ile—OH   13

11 $\xrightarrow{((C_6H_5)_3P)_4Pd/THF}$    14

Z—Tyr(Bzl)—Gly—Gly—Phe—Leu—OH

The dissolved off products for example 12 (Example 7), 13 (Example 8) and 14 (Example 9), can be isolated in good yields, selectively or partly protected. Therefore, they can be used immediately for further syntheses, such as precise fragment condensations. They can naturally also be freed from the remaining protective groups.

The carriers according to the present invention, such as, for example 5, which rake possible the solid phase synthesis of peptides and glycopeptides via constructional units bound to the carrier as (substituted) allyl esters, thus have decisive advantages: they are simple to build up and permit an effective, racemisation-free coupling on of the C-terminal constructional unit. The solid phase peptide synthesis can be carried out with acid- and base-labile amino protective groups. Very effective splitting off of the synthesised peptides or glycopeptides is possible under almost neutral conditions; sensitive structural elements, for example glycoside bonds and acid- (e.g. Boc) and baselabile (e.g. OAc) protective groups are thereby not attacked. The following Examples are given for the purpose of illustrating the present invention:

EXAMPLE 1

Synthesis of an activated or activatable polymeric carrier with allylic anchor groups of general formula (I)

N-(4-Bromocrotonyl)-aminomethyl-polystyrene (5)

2 g. Arinomethylpolystyrene (3) (0.8 mole equiv. $NH_2/g$ of resin) are stirred in 40 ml. anhydrous dichloromethane with 1.02 g. (6.2 mmole) 4-bromocrotonic acid, 0.2 g. (1.65 mmole) 4-dimethylaminopyridine and 1.53 g. (7.5 mmole) N,N'-dicyclohexylcarbodiimide for 12 hours at ambient temperature. The polymer is then filtered off over a D3 frit, washed with dichloromethane, methanol and dimethyl formamide and again with dichloromethane and dried at 30° C. in a high vacuum.

In the IR spectrum, the polymeric material shows those bands which indicate the reaction to the product (5) with the allylic anchor group:

IR (KBr): $\nu(cm^{-1})$ =3300 (NH);1670 (amide I),970 (C—CH=CH=)

EXAMPLE 2

Coupling of a C-terminal amino acid to the polymeric carrier:

N-tert.-Butyloxycarbonyl-L-alanyl-(4-hydroxycrotonyl- amidomethyl)-polystyrene (7)
(N-Boc-Ala-"Hycram" polystyrene)

1.59 mmole of the N-protected amino acid (in Example 2 tert.-butyloxycarbonyl-L-alanine) is stirred in 30 ml. methanol with 0.26 g. (0.79 mmole) caesium carbonate for 2 hours at ambient temperature. The solvent is then evaporated off and anhydrous toluene distilled off several times from the remaining cesium salt (here 6). The so obtained cesium salt is now stirred with 0.9 g. of the polymeric carrier with the allylic anchor group prepared according to Example 1 for 24 hours in 50 ml. dimethylformamide. The resulting coupling product 7 is then filtered off, washed with dimethyl formamide, dioxan and dichloromethane and dried in a vacuum at 30°–35° C.

The Hycram- (4-hydroxycrotonylamidomethyl) poly- styrene-bound Boc-alanine shows in the IR spectrum the additional IR bands: IR (KBr): $\nu(cm^{-1})$ =1740 (C—0, ester); 1710 -1700 (C=0, urethane).

The following two Examples show the typical reaction cycle which is carried out in the case of peptide and glycopeptide syntheses on carrier systems according to the present invention with allylic anchor groups in the case of each chain elongation.

EXAMPLE 3

Splitting off of the N-terminal protective group and splitting off of the tert.-butyloxycarbonyl group from the Hycram-polystyrene-bound Boc-alanine Alanyl-Hycram-polystyrene (8)

The Boc-alanyl-Hycram-polystyrene 7 (1.3 g.) synthesised according to Example 2 is shaken with 20 ml. 50% trifluoroacetic acid in dichloromethane for 1.5 hours. Thereafter, it is filtered off, shaken 4 times with anhydrous dichloromethane and filtered off. The so-obtained hydro-trifluoroacetate of the polymer-bound alanine 8 is shaken twice with 0.5 ml. ethyl-diisopropylamine in 10 ml. dichloromethane, in each case for 10 minutes, filtered off and subsequently shaken twice with anhydrous dichloromethane and filtered.

In the IR spectrum of the product 8, the typical urethane band ($\nu=1710-1700$ cm$^{-1}$) is no longer present.

EXAMPLE 4

Chain elongation of any aminoacyl or peptide constructional unit bound via an allylic anchor group to the polymeric carrier Boc-leucyl-alanyl-Hycram-polystyrene (9)

1.02 g. of the polymer-bound alanine 8 prepared according to Example 3 are shaken for 12 hours at ambient temperature in 30 ml. anhydrous dichloromethane with 0.87 g. (3.7 mmole) Boc-leucine, 0.93 g. (4.5 mmole) dicyclohexylcarbodiimide and 0.1 g. (0.75 mmole) 1-hydroxybenzotriazole.

The polymer-bound dipeptide 9 is filtered off, washed with dichloromethane, dimethylformamide and again with dichloromethane and dried.

EXAMPLE 5

Synthesis of an N-glycopeptide on the polymeric carrier

Boc-leucyl-[$N^4$-(2-acetamido-3,4,6-tri-0-acetyl-2-desoxy-$\beta$-D-glucopyranosyl)]-asparaginyl-isoleucyl-Hycram-polystyrene (10)

Corresponding to the procedure described in the Examples 2–4, from 0.32 g. bromocrotonylamidomethylpolystyrene 5 and 0.32 g. (1.38 mmole) Boc-isoleucine, there is first prepared, via the cesium salt, the Boc-L-isoleucyl polymer. This is N-terminally unblocked with trifluoroacetic acid/dichloromethane and the terminal ammonium group is deprotonised with 40 ml. 5% ethyl-diisopropylamine in dichloromethane:

The chain elongation is carried out with $N^2$-tert.-butyloxycarbonyl-[$N^4$-(2-acetamido-3,4,6-tri-0-acetyl-2-desoxy-$\beta$-D-glucopyranosyl)]-L-asparagine (0.34 g. = 0.6 mmole) analogously to Example 4. The N-terminal unblocking and the chain elongation is now repeated correspondingly with tert.-butyloxycarbonyl-L-leucine (0.43 g. = 1.85 mmole). All washing and drying steps are carried out according to the procedure in Example 4. There is thus obtained the glycotripeptide 10 bound via the allylic anchor group to the polymer.

EXAMPLE 6

Synthesis of terminal-protected Leu-encephaline on the polymeric carrier.

Z-Tyr(Bzl)-Gly-Gly-Phe-Leu-Hycram-polystyrene (11).

According to the steps described in the Examples 2–4, 1.41 g. (3.9 mmole) Boc-leucine is first reacted via the cesium salt with 1 g. 4-bromocrotonylamido-(BCA)-polystyrene 5 (Example 1). The Boc protective group is split off from the coupling product obtained with 50% trifluoroacetic acid in dichloromethane. The terminally unblocked leucine bound to Hycram-polstyrene is now attached to 1.03 g. (3.9 mmole) Boc-phenylalanine in the presence of 0.96 g. (4.7 mmole dicyclohexylcarbodiimide and 0.1 g. (0.74 mmole) 1-hydroxybenzotriazole in 30 ml. dichloromethane.

There follow further synthesis cycles of Boc group splitting off, deprotonisation and coupling twice with 0.68 g. (3.9 mmole) Boc-glycine and with 1.57 g. (3.9 mmole) Z-(0-benzyl)-tyrosine, the couplings thereby being carried out in each case with the same amounts of dicyclohexylcarbodiimide and 1-hydroxybenzotriazole in these three cycles in 30 ml. anhydrous dimethylformamide. The polymer-bound pentapeptide 11 obtained according to the present invention is then used for the dissolving off from the polymer (Example 9).

EXAMPLE 7.

Splitting off of the peptide from the polymeric carrier according to the present invention tert.-Butyloxycarbonyl-L-leucyl-L-alanine (12)

The Boc-leucyl-alanine 9 (prepared according ro Example 4) bound to Hycram-polystyrene (1.15 g.) is shaken for 2 hours at ambient temperature in 50 ml. oxygen-free tetrahydrofuran under nitrogen with 4 ml. morpholine and 0.1 g. tetrakis-(triphenylphosphino)-palladium-(O). The resin is filtered off and washed several times with dichloromethane and with methanol. The combined organic solutions are freed from the solvents in a vacuum and the residue taken up in 70 ml. dichloromethane and shaken out several times with 20% citric acid. The organic phase is then extracted three times with 30 ml. saturated aqueous sodium bicarbonate solution, the aqueous phase adjusted to pH 1.5 and shaken out 6 times with 30 ml. dichloromethane. The combined dichloromethane solutions are dried over anhydrous sodium sulphate and freed from solvent in a vacuum. As residue, there remain 130 mg. tert.-butyloxy- carbonyl-L-leucyl-L-alanine 12 (80% of the maximum obtainable amount referred to the reactive 4-bromocrotonylamido groups on the resin 5). $R_f$=0.15 (chloroform/methanol 5:1).

400 MHz-$^1$H-NMR (CDCl$_3$): $\delta$=7.13 (m, 1H, NH, Ala); 5.35 (m, 1H, NH, urethane); 4.53 (m, 1H, $\alpha$-CH, Ala); 4.22 (m, 1H, $\alpha$-CH, Leu); 1.75–1.53 (m, 3H, CHHD 2—CHCH$_3$)$_2$, Leu); 1.40 (m, 12H, CH$_3$ from Boc, Ala); 0.95 –0.83 (m, 6H, CH$_3$, Leu).

EXAMPLE 8

Splitting off of a glycopeptide from the polymeric carrier

N-tert.-Butyloxycarbonyl-L-leucyl-[$N^4$-(2-acetamido3,4,6-tri-0-acetyl-2-desoxy-$\beta$-D-glucopyranosyl)]- L-asparginyl-L-isoleucine (13)

0.5 g. of the polymer-bound glycopeptide 10 are shaken under nitrogen with 2 ml. morpholine and 0.1 g. tetrakis-(triphenylphosphino)-palladium (O) in 30 ml. tetrahydrofuran for 12 hours. The resin is filtered off and then washed with tetrahydrofuran and methanol. The combined organic solutions are evaporated in a vacuum and the residue is chromatographed in dichloromethane/methanol (12/1) over silica gel to give 70 mg. (50% of the maximum obtainable amount) of the glycotripeptide 13. $R_f$=0.29 (dichloromethane methanol 5:1).

400 MHz-$^1$H-NMR (dimethyl sulphoxide-d$_6$) $\delta$=8.72 (d, J=10 Hz, 1H, $\beta$-NH, Asn); 8.32 (m, 1H, $\alpha$-NH, Asn); 7.99 (d, broad, J=10 Hz, 1H, NH-Ac); uns/H/-Ac); 7.08 (m, 1H, NH, Ile); 6.9 (d, J=$\overline{10}$ Hz, 1H, NH, urethane, Leu); 5.25–5.11 (m, 2H, H-1, H-3); 4.85 –4.75 (m, 1H, H-4); 4.62 (m, 1H, $\alpha$-CH, Asn); 4.25 –4.10 (m, 2H, H-6a, $\alpha$-CH-Ile); 4.03 –3.87 (m, 2H, H-6b, H-2 or H-5); 2.75 (m, 1H, $\beta$-CH$_2$, Asn); 2.25 (m, 1H, $\beta$-CH$_2$, Asn); 2.0 (s, 3H, AcO, sugar); 1.95 (s, 3H, AcO, sugar); 1.92 (s, 3H, AcO, sugar); 1.73 (s, broad, 4H, AcNH, sugar, $\beta$-CH, Ile); 1.65 –1.52 (m, 2H, CHHD 2, Leu); 1.34 (s, broad, 11H, CH$_3$ from Boc, C$\overline{H_2}$-CH Leu, 1H CHHD 2-CH$_3$, Ile); 1.1 –0.95 (m, 1H, 1H from CHHD 2-$\overline{C}$H$_3$, Ile); 0.88 (m, 12H, CH$_3$ from Leu (2×) and Ile (2×)).

EXAMPLE 9

Splitting of of a peptide active material from the polymeric carrier according to the present invention
Protected Leu-encephaline 14

1.7 g. of the polymer-bound N-terminal Z- and 0benzyl ether-protected Leu-encephaline 11 is shaken under nitrogen with 10 ml. morpholine and 0.1 g. tetrakis-(triphenylphosphino)-palladium-(O) for 10 hours in 50 ml. tetrahydrofuran. It is then filtered off from the polymers, thoroughly washed with tetrahydrofuran and methanol and the combined organic solutions are evaporated in a vacuum.

The purification takes place by repeated reprecipitation from chloroform/diethyl ether, the product being obtained as gel by centrifuging off. As yield, there is obtained 150 mg. of the protected Leu-encephaline (33% of the maximum obtainable amount).

400 MHz-$^1$H-NMR (dimethyl sulphoxide-$d_6$): $\delta = 8.5$ (d, J=8 Hz, 1H, NH); 8.39 (m, 1H, NH, Gly); 8.17 (d, J=8 Hz, 1H, NH); 8.08 (m, 1H, NH, Gly); 7.54 (d, J =8 Hz, NH, Tyr); 7.46–7.05 (m, 17H, aromatics: Phe, Z, Bzl, 2H from Tyr); 6.88 (d, J = 10 Hz, 2H, 2H from Tyr); 5.03 (s, 2H, CH2 from Z); 4.96 –4.84 (m, 2H, CH2 from Bzl); 4.53 (m, 1H, α-CH, Leu); 4.29– 4.14 (m, 2H, α-CH, Tyr; α-CH, Phe); 2.82 –2.62 (m, 2H, CH2, Thyr); 1.65 1.54 (m, 2H, CH2, Leu); 1.48 (m, 1H, -CH-CH 3, Leu); 0.88 (d, J =7 Hz, 3H, CH3, Leu); 0.82 (d, J =7 Hz, 3H, CH3, Leu).

We claim:

1. A solid phase system comprising allylic side chains bound to a solid carrier material, said system having the formula:

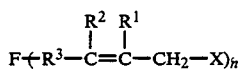

wherein F is a solid carrier material, $R^1$ and $R^2$ are hydrogen atoms, halogen atoms, alkyl radicals or aryl radicals, $R^3$ is a linking group or spacer, X is hydroxyl, halogen, sulphonate, phosphonate or acyloxy radical containing a residue of an aliphatic carboxyl acid or RCO-, wherein R is an organic radical bound to the carbonyl group, and n is the number of allylic side chains bound to said carrier material.

2. The solid phase system of claim 1, wherein RCO- is a residue of an amino acid, peptide, glycopeptide, nucleotide hydrocarboxylic acid, icarboxylic acid or tricarboxylic acid.

3. The solid phase system of claim 1 wherein said solid phase carrier material is a polymer.

4. The solid phase system of claim 1, wherein said solid carrier material is coated with a second material which links with said allyl side chain.

5. The solid phase system of claim 3, wherein said polymer is a cross-linked polystyrene.

6. The solid phase system of claim 5, wherein said polystyrene carries an aminomethyl radical.

7. The solid phase system of claim 2, wherein said residue is a protected residue.

8. The solid phase system of claim 2, wherein said residue is an unprotected residue.

9. The solid phase system of claim 3, wherein said polymer is an organic polymer.

10. The solid phase system of claim 3, wherein said polymer is an inorganic polymer.

11. The solid phase system of claim 4, wherein second material is a cross-linked polystyrene.

12. The solid phase system of claim 11, wherein said polystyrene carries an aminomethyl radical.

13. The solid phase system of claim 6, wherein $R^3$ is —CO—(—CH2)$_a$ where a is a whole number from 0 to 7.

14. The solid phase system of claim 12, wherein $R^3$ is —CO—(—CH2)$_X$ where X is a whole number from 0 to 7.

15. Process for the preparation of a solid phase system of formula:

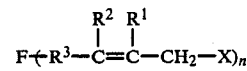

wherein F is a solid carrier material $R^1$ and $R^2$ are hydrogen atoms, halogen atoms, alkyl radicals or aryl radicals, $R^3$ is a linking group or spacer, X is hydroxyl, halogen, sulphonate, phosphonate or acyloxy containing a reacting a solid carrier material containing a functional group A which links with an alkyl radical —$CR^2$=$CR^1$—CH2-X with a compound of formula B—$CR^2$=$CR^1$—CH2-X, where $R^1$, $R^2$ and X are as defined above, and A and B are groups which react with one another by at least one of condensation and addition to form a linking groups $R^3$ between the solid carrier material and the allyl radical.

16. Process of claim 15 wherein the solid phase cararier material containing A is an aminomethylated polystyrene, and B-$CR^2$=$CR^1$-CH2-X is one of a terminally allylic substituted unsaturated carboxylic acid, a carboxylic acid derivative or a 1,3-allyl isomer thereof.

17. Process of claim 16 wherein B—$CR^2$=$CR^1$—$^{CH_2}$-X is an allylic-substituted carboxylic acid selected from the group consisting of 4-halo, 4hydroxy, 4-acyloxy and 4-sulphonyloxy - crotonic acid.

18. Process of claim 15, further comprising reacting X with an N-protected amino acid, an N-protected peptide, an N-protected glycopeptide, or a nucleotide, a hydroxycarboxylic acid a dicarboxylic acid, a tricarboxylic acid derivatives or a salt theroef.

19. Process of claim 18, comprising reacting X with an N-protected substance selected from the group consisting of an N-protected amino acid, N-protected peptide, and an N-protected glycopeptide.

20. Process of claim 19, further comprising treating said N-protected substance to remove the protective group therefrom.

21. Process for the synthesis of an unprotected or a partly protected peptide, glycopeptide, nucleotide, dicarboxylic acid, or tricarboxylic acid, comprising, reacting a compound of formula:

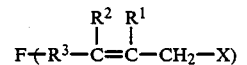

where F is a solid carrier material, $R^1$ and $R^2$ are hydrogen, halogen, alkyl radicals or aryl radicals, $R^3$ is a linking group or spacer, and X is an acyloxy radical containing RCO—, wherein R is a protected residue of a peptide, a glycopeptide, a nucleotide, a hydroxycarboxylic acid, a dicarboxylic, or a tricarboxylic acid in the presence of a catalytic amount of a palladium metal compound to split said RCO— radical therefrom.

* * * * *

UNITED STATES PATENT AND TRADEMARK OFFICE
CERTIFICATE OF CORRECTION

PATENT NO. : 4,929,671

DATED : May 29, 1990

INVENTOR(S) : Horst Kunz et al

It is certified that error appears in the above-identified patent and that said Letters Patent is hereby corrected as shown below:

Column 1, line 13, "peptides this" should read --peptides. This--.

Column 1, line 29, "used" should read --uses--.

Column 1, line 61, "B$^2$" should read --R$^2$--.

Column 2, line 23, "usefull" should read --useful--.

Column 2, line 37, "R3" should read --R$^3$--.

Column 2, line 67, delete "be".

Column 3, line 21, after "groups" insert --.--.

Column 4, line 3, "flurenylme-" should read --fluorenylme- --.

Column 5, line 2, "used" should read --use--.

Column 7, line 35, before "the" insert --From--.

Column 9, line 42, "rake" should read --make--.

Column 9, line 62, "Arino" should read --Amino--.

Column 10, line 7, "(C-CH=CH=)" should read --(C-CH=CH-)--.

Column 12, line 21, "C$\underline{H}$HD 2-C$\underline{H}$CH$_3$)$_2$" should read --C$\underline{H}_2$-C$\underline{H}$(CH$_3$)$_2$--.

UNITED STATES PATENT AND TRADEMARK OFFICE
CERTIFICATE OF CORRECTION

PATENT NO. : 4,929,671

DATED : May 29, 1990

INVENTOR(S) : Horst Kunz et al

It is certified that error appears in the above-identified patent and that said Letters Patent is hereby corrected as shown below:

Column 12, lines 44 to 45, delete "uns/H/-Ac);".

Column 12, line 52, "CHHD 2" should read --$\underline{CH}_2$--.

Column 12, line 54, "CHHD 2" should read --$\underline{CH}_2$--.

Column 13, line 17, "-CH-CH 3" should read -- -$\underline{CH}$-$CH_3$--.

Column 12, line 59, "of of" should read --off of--.

Column 13, line 41, "icarboxylic" should read --dicarboxylic--.

Column 14, line 18, after "a" first occurrence, insert --residue of an aliphatic carboxyl acid and, n is the number of allylic side chains bound to said solid carrier material comprising--.

Signed and Sealed this

Fifth Day of May, 1992

Attest:

DOUGLAS B. COMER

Attesting Officer

Acting Commissioner of Patents and Trademarks